(12) United States Patent
Reiner

(10) Patent No.: US 6,212,006 B1
(45) Date of Patent: Apr. 3, 2001

(54) STEREOSCOPIC MICROSCOPE

(75) Inventor: Josef Reiner, Cologne (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 0 days.

(21) Appl. No.: 09/543,720

(22) Filed: Apr. 5, 2000

(30) Foreign Application Priority Data

Apr. 8, 1999 (DE) .............................. 299 05 969

(51) Int. Cl.$^7$ ............................ G02B 21/06; G02B 21/00
(52) U.S. Cl. ........................ 359/388; 359/368; 359/370
(58) Field of Search ................................ 359/368–389; 351/219, 229–236, 245, 247; 600/101–102, 166, 172

(56) References Cited

U.S. PATENT DOCUMENTS

| 4,253,726 | * | 3/1981 | Taira | 359/388 |
| 4,710,000 | * | 12/1987 | Spitznas et al. | 359/377 |
| 5,282,085 | * | 1/1994 | Volkert et al. | 359/377 |
| 5,438,456 | * | 8/1995 | Grinblat | 359/380 |
| 5,793,524 | * | 8/1998 | Luloh | 359/380 |

FOREIGN PATENT DOCUMENTS

| 38 26 069 | 2/1990 | (DE) . |
| 298 19 341 | 3/1999 | (DE) . |
| 98/20378 | 5/1998 | (WO) . |

* cited by examiner

*Primary Examiner*—Thong Nguyen
(74) *Attorney, Agent, or Firm*—Flynn, Thiel, Boutell & Tanis, P.C.

(57) ABSTRACT

A stereoscopic microscope includes a binocular eyepiece arrangement, a binocular magnification changer, and a monocular lens arrangement. A reversal lens system can be inserted into beam paths in front of or behind the magnification changer, whereby it exchanges the two beam paths against one another and at the same time causes an image reversal. Thus, the microscope enables quick and simple changing between two focusings of the microscope without limiting the operation of the magnification changer. A supplementary lens can be inserted on the input side of the lens arrangement into the beam paths and an optic system can be inserted into the beam path between the supplementary lens and the eye for wide-angle viewing of the retina. The supplementary lens is a convex lens, the focal length of which is chosen in such a manner that the retina can be viewed with the microscope through the inserted supplementary lens and the optic system, while the lens arrangement of the microscope is focused on the cornea.

15 Claims, 3 Drawing Sheets

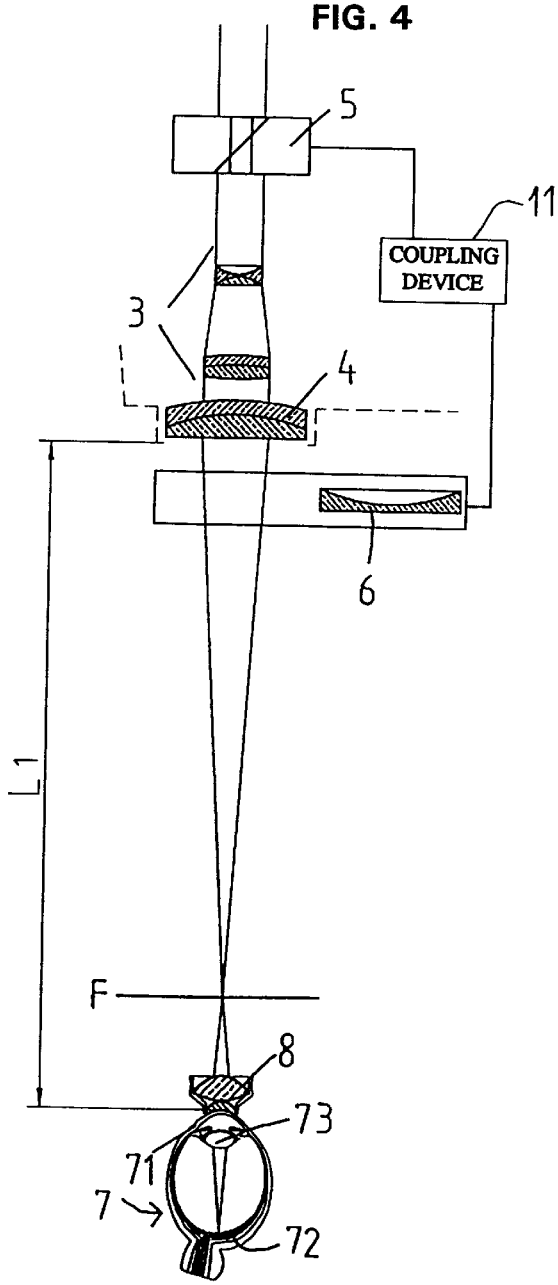
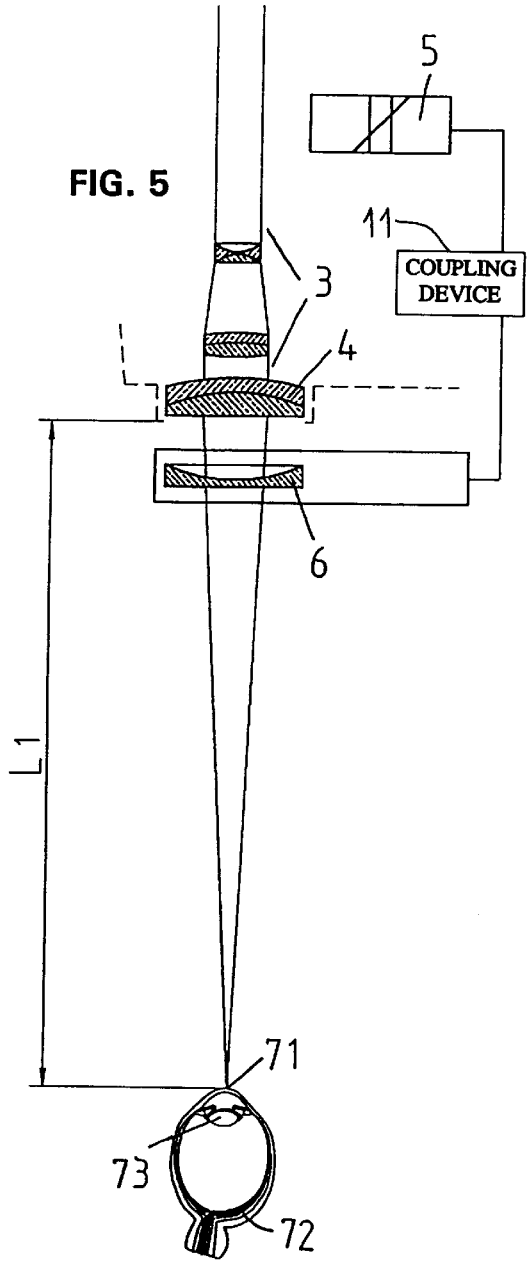

STEREOSCOPIC MICROSCOPE

FIELD OF THE INVENTION

The invention relates to a stereoscopic microscope, in particular for eye examinations in ophthalmology, or other medical sciences, comprising a binocular lens arrangement, a binocular magnification changer, and a monocular lens arrangement, whereby a reversal lens system can be moved into the beam paths in front of or behind the magnification changer, and the reversal lens system exchanges the two beam paths against one another and causes at the same time an image reversal.

BACKGROUND OF THE INVENTION

Such a microscope is known, for example, from German Patent DE 38 26 069 C2. In carrying out diagnostic services or surgeries using a stereoscopic microscope, for example in ophthalmology, neurosurgery, etc., microscopes with a weak enlargement are usually being used. These have separate beam paths in order to enable a stereoscopic viewing of the surgery field. Ocular systems are thereby used, each including an ocular tubus forming a telescope. Furthermore, a common lens is used for both beam paths, in which lens is provided in most cases a common convex lens.

The beams or rays enter in such a microscope through the lens. The beams are guided parallel through the lens systems and are fed to the magnification changer. The beams exit from the changer and are in turn focused in parallel and fed to the respective ocular system or tubus.

In viewing the inside of the eye, one must note that due to the lens of the eye itself a laterally transposed image of the inside of the eye is viewed by the microscope. In order to eliminate this transposition or reversal, and in order to show tne image in the correct manner, an image reversal and also a change of the beam paths, namely an exchange of the right and left beam path, must be carried out in the area of the microscope. The reversal lens system provided in the microscope is used for this purpose.

It is often necessary during an eye surgery or examination that the viewer alternately view two well defined areas of the inside of the eye. The focal point of the lens must thereby be shifted in the presently existing microscopes through new focusing. The new focusing requires in each case some seconds. In particular, in the case of longer surgeries or also eye examinations, the time needed for the refocusing at a repeated change of the viewing planes cannot be neglected.

This problem occurs in particular also when an optic system is used, as is known, for example, from DE 298 19 341.8. Such an optic system is used to view the fundus of the eye, in particular of the retina. The optic system creates a first image in a point in front of the optic system. In order for the viewer to be able to view through the microscope this first image created in front of the optic system, the lens of the microscope must be focused onto this first image.

When the viewer now wants to change between the viewings with the optic system or without the optic system, the microscope must, after the optic system has been removed from the beam path, be newly focused. Thus a new focusing is necessary with each change of viewing with or without the optic system. A microscope is known from WO 98/20378, in which above and/or below the reversal lens system together with said reversal lens system lenses are moved into the beam path, which change the focusing of the microscope so that, when an optic system is inserted into the beam path, the image created in front of the optic system can be clearly recognized. A magnification changer is interpositioned in most stereoscopic microscopes so that it is possible to pull also smaller cutouts enlarged from an image. Tf a reversal lens system with a fixedly attached lens is now swung into the parallel beam path, then the compensation of the distance between the earlier focused point and the image created before the optic system, which compensation is caused by the fixedly attached lens, can be utilized only for a very specific adjustment in the magnification changer. The reason or cause for this is that the parallel beam path is changed in the reversal lens system by inserting the lenses. Whereas if travel occurs in all possible areas through the magnification changer, then a blurred, not usable image is created in almost all areas through the decentration.

SUMMARY OF THE INVENTION

The basic purpose of the invention is therefore to provide a microscope, in which a quick and simple change between two focusings or focal lengths of the microscope is possible. This invention will not limit the operation or function of the magnification changer.

This purpose is attained according to the invention by a supplementary lens that can be inserted or swung into the beam paths on the input side of the lens arrangement, and an optic system that can be inserted between the supplementary lens and the eye into the beam path for wide-angle viewing of the retina. The supplementary lens can be a convex lens having a focal length chosen in such a manner that the retina can be viewed with the supplementary lens and the optic system inserted or swung in the beam path, while the lens arrangement of the microscope is focused on the cornea.

By inserting or swinging in the supplementary lens it is possible to change the focal length of the microscope in such a manner that the viewer, depending on the position of the supplementary lens and the optic system, can view the retina or the cornea of the eye. The supplementary lens is a convex lens, the focal length of which is chosen in such a manner that the inside of the eye can be viewed with the microscope, with the supplementary lens being inserted or swung in, and the optic system is moved in, while the lens of the microscope is focused on the cornea. When the optic system is now removed from the beam path between the eye and the lens and also the supplementary lens is again moved out of the beam path, it is possible without a new focusing of the lens of the microscope to clearly view the cornea directly. A new focusing of the microscope is thereby no longer necessary. The advantage of the inventive arrangement of the supplementary lens is mainly that independent of the position of the supplementary lens, positioned or not positioned in the beam path, the magnification changer can be fully utilized.

The reversal lens system and the supplementary lens are then advantageously coupled with one another mechanically, electromechanically and/or electronically so that the reverse lens system and the supplementary lens can be simultaneously inserted or swung into the beam path. This coupling offers an advantage during the following procedure or process. The cornea is first directly viewed by means of the microscope. Whereas if the inside of the eye is supposed to be viewed, for example, with the help of the optic system, an image exchange and reversal occurs due to the optic system so that the image is recognized laterally transposed and upside down by the viewer. The reversal lens system must then be inserted into the beam paths so that the image can be recognized laterally correct. By means of a device, through which the supplementary lens and the reversal lens system are simultaneously swung in and out, it is now possible to prepare the microscope with one manipulation in order to view, after viewing the cornea, the inside of the eye by means of an optic system.

A further attainment of the purpose is that an optic system can be inserted into the beam path between the lens arrangement and the eye being tested for wide-angle viewing of the retina, which optic system reproduces a first image, which can be viewed with the microscope, at a point between the lens arrangement and the optic system, and that the microscope has a supplementary lens, which can be inserted or swung into the beam path, on the input side of the lens arrangement, whereby the supplementary lens is a dispersing lens, having a focal length so that the cornea can be viewed through the microscope with the supplementary lens inserted or swung-in, while the lens arrangement of the microscope is focused on the point of the first image.

The inside of the eye is first viewed by means of an optic system in this stereoscopic microscope. An image of the inside of the eye is thereby created in front of the optic system. The microscope is now adjusted to this image created before the optic system. When the optic system is now removed from the beam path between the microscope and the eye tested in order to be able to view the cornea of the eye, then the supplementary lens, which is a dispersing lens, is inserted into the beam path. The focal length of the microscope is changed in this manner so that the cornea can be clearly recognized through the microscope.

The reversal lens system is again inserted into the beam path for viewing the image by means of the optic system so that the image can be recognized laterally correct. When viewing the cornea it is necessary to remove the reversal lens system again from the beam path and to position the supplementary lens into the beam path in exchange therefor. It is therefore advantageous that the reversal lens system and the supplementary lens are coupled with one another mechanically, electromechanically and/or electronically so that the supplementary lens and the reversal lens system can be inserted or moved only alternately into the beam path.

It is advantageous for the up to now described stereoscopic microscope when the supplementary lenses are mounted exchangeably in the microscope.

BRIEF DESCRIPTION OF THE DRAWINGS

One exemplary embodiment will be described in greater detail in connection with the drawings, in which:

FIG. 4 is a side view of a further microscope of the invention with a supplementary lens inserted into the beam path, and FIG. 5 illustrates the microscope the supplementary lens not inserted into the beam path.

DETAILED DESCRIPTION

Figure 1:
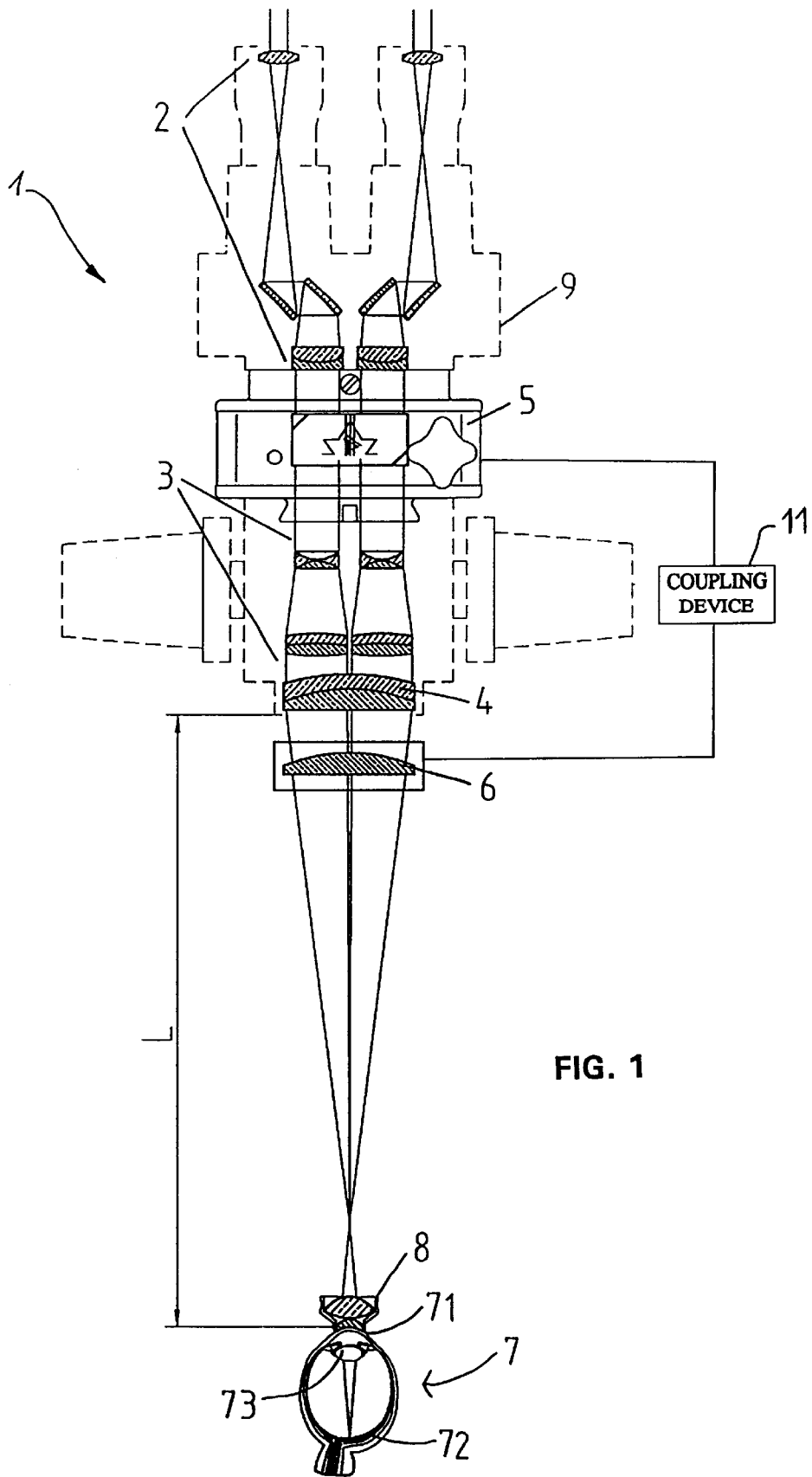
FIG. 1 illustrates a sectional view of a microscope of the invention with an insertable supplementary lens.

The microscope 1 of the invention illustrated in FIG. 1 includes an eyepiece arrangement 2, which is followed by a reversal lens system 5. The beam path continues through a magnification changer 3, followed by a lens arrangement 4 and finally a supplementary lens 6. An optic system 8 is arranged between the supplementary lens 6 and an eye 7 to be examined, which system 8 is placed directly onto the eye. The microscope 1 is enclosed in the usual manner by a housing 9, which is only schematically illustrated. Such a microscope 1 is, with the exception of the supplementary lens 6, known from the state of the art, in particular from DE 38 26 069.7, so that the further description relates essentially to the inventive arrangement of the supplementary lens 6.

Figure 2:
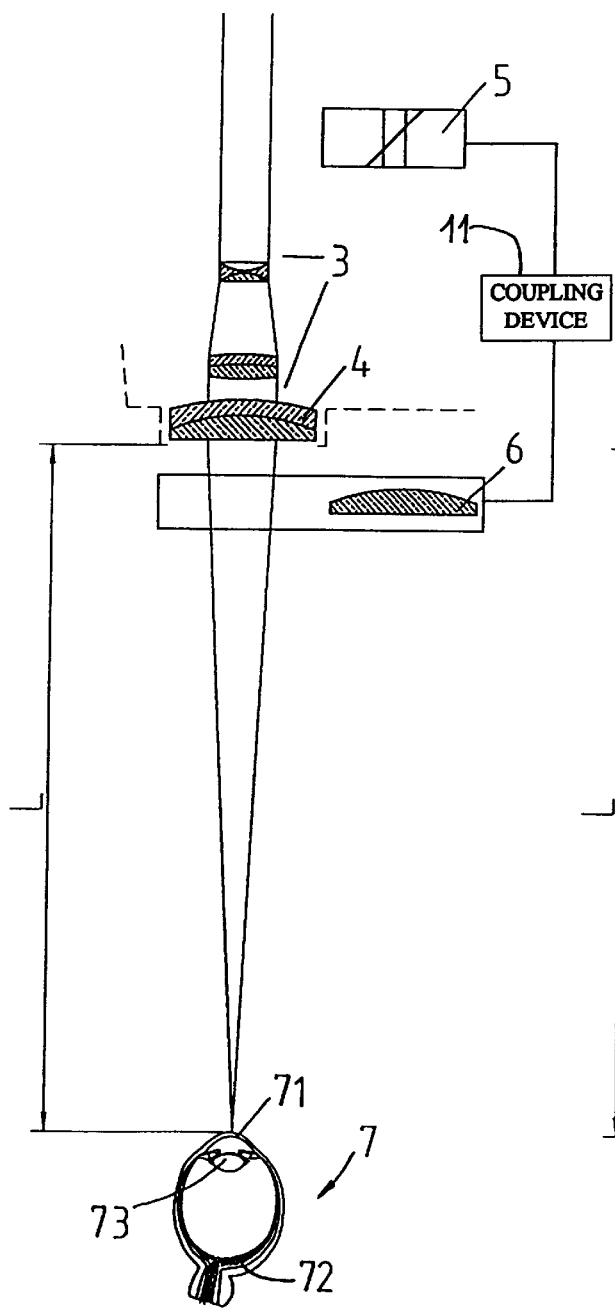
FIG. 2 is a side view of the microscope of FIG. 1 with the supplementary lens not inserted into a beam path.
Figure 3:
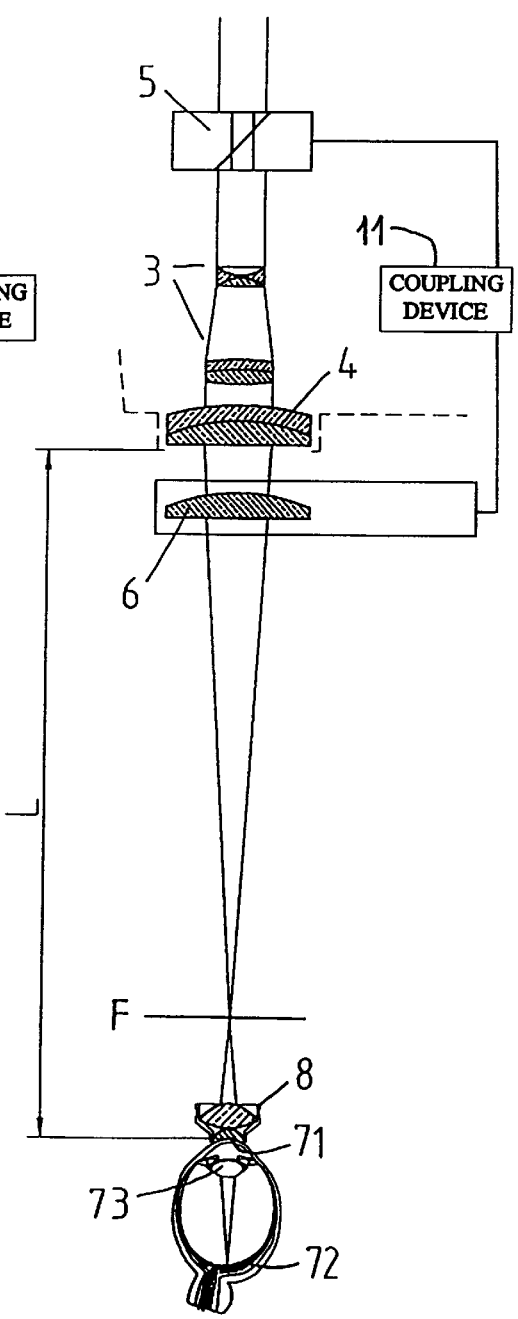
FIG. 3 is a side view of the microscope of FIGS. 1 and 2 with the supplementary lens inserted into the beam path.

A convex lens is provided as the supplementary lens 6 in the microscope according to FIG. 1. The operation of this convex lens 6 will now be described in connection with FIGS. 2 and 3. FIGS. 2 and 3 each show a schematic cross section of a side view of the microscope 1 according to FIG. 1. The microscope 1 is shown starting from the reversal lens system 5 downwardly. The cornea 71 of the eye 7 can be viewed with an arrangement according to FIG. 2. For this purpose, the supplementary lens 6 is initially swung or moved out of the beam path. The lens 4 of the microscope 1 is adjusted such that the cornea 71 lies in the focal point of said lens 4. Since the eye 7 is not viewed through an optic system 8, image exchange and image reversal does not occur. Accordingly, also the reversal lens system 5 is moved or swung out of the beam path. The reversal lens system 5 and the supplementary lens 6 are coupled with one another at least one of mechanically, electromechanically or electronically, by a coupling device 11. Thus, the reversal lens system 5 and the supplementary lens 6 shown in FIGS. 2 and 3 are capable of simultaneous insertion and removal from the beam path of the microscope. Whereas in the arrangement according to FIG. 3 an optic system 8 is placed onto the cornea 71 of the eye 7. This optic system, which is known, for example, from DE 298 19 341.8, is used to view the retina 72 through the lens 73 of the eye 7. A first image of the retina 72 can be clearly recognized in the point F. By swinging the convex lens 6 into the beam path of the microscope 1, the focal length of the microscope is shortened so that the focal point of the microscope 1 coincides now with the point F of the first image. Thus the viewer can clearly recognize the image of the retina 72. Since the viewing of the eye 7, however, occurs through the optic system 8, the viewer recognizes a laterally transposed and reversed image of the retina 72. Here help can be given by inserting the reversal lens system 5, as it is already illustrated in FIG. 3.

In contrast to the microscope 1 illustrated in FIGS. 1 to 3, the microscope 1, which is illustrated in FIGS. 4 and 5, has a dispersing lens as the supplementary lens 6. This dispersing lens 6 has the effect that the focal length of the microscope 1 is enlarged. The retina 72 of the eye 7 is in the arrangement according to FIG. 4 when first viewed with the help of the optic system 8. A first image of the retina is thereby created in the point F before the optic system 8. The microscope 1 is, with the dispersing lens 6 moved or swung out of the beam path, adjusted and focused to this point F. The viewer thus reacquires a clear image of the retina 72 through the lens 73 of the eye. Since the retina 72 lies behind the optic system 8, the viewer recognizes a reversed and laterally transposed image when the reversal lens system 5, as illustrated in FIG. 4, is not moved or inserted into the beam path. When the optic system 8 is now removed from the beam path in order to view the cornea 71 of the eye 7, the focal length of the microscope 1 is too short in order to recognize a clear image. In order to recognize a clear image, the dispersing lens 6 is now inserted into the beam path and the focal length of the microscope 1 is lengthened in this manner. The strength of the dispersing lens 6 is thereby chosen in such a manner that, after insertion of the same, a clear image of the cornea 71 is created in the eye of the viewer. A reversal and lateral transposition of the image is also no longer necessary. Consequently the reversal lens system 5 is no longer positioned or swung into the beam path. The reversal lens system 5 and the supplementary lens 6 are coupled with one another at least one of mechanically, electromechanically or electronically, by a coupling device 12. Thus, the reversal lens system 5 and the supplementary lens 6 shown in FIGS. 4 and 5 are alternately inserted into the beam path of the microscope.

It is possible to switch in a simple and quick manner between the viewing of various areas of the eye 7 with the two described arrangements according to FIGS. 1 to 3 or 4 and 5. In order to obtain thereby each one laterally correct clear image, the supplementary lens 6 or the reversal lens system 5 must be swung into or out of the beam path.

What is claimed is:

1. A stereoscopic microscope comprising: a binocular lens arrangement, a binocular magnification changer, a monocular lens arrangement, and a movable reversal lens system for selective insertion into two beam paths in front of or behind the magnification changer, the reversal lens system exchanging the two beam paths against one another and causing at the same time an image reversal, the improvement comprising a supplementary lens for selective insertion or movement into an input beam path on an input side of the lens arrangement, and an optic system for selective insertion into the input beam path between the supplementary lens and an eye being tested for wide-angle viewing of a retina, the supplementary lens comprising a convex lens having a focal length being chosen or preselected so that the retina is viewable through the supplementary lens and the optic system of the microscope, while the lens arrangement of the microscope is focused on the cornea.

2. The microscope according to claim 1, wherein the reversal lens system and the supplementary lens are coupled with one another at least one of mechanically, electromechanically or electronically so that the reversal lens system and the supplementary lens are capable of simultaneous insertion into the beam paths and the input beam path, respectively.

3. A stereoscopic microscope for use in ophthalmology examinations, comprising: a binocular lens arrangement, a binocular magnification changer, a monocular lens arrangement, and a reversal lens system for insertion or movement into two beam paths in front of or behind the magnification changer, the reversal lens system exchanging the two beam paths against one another and causing simultaneously an image reversal, an optic system for selective insertion into an input beam path between the lens arrangement and an eye under examination for wide-angle viewing of a retina, the optic system reproducing a first image for viewing with the microscope at a point between the lens arrangement and the optic system, the microscope including a supplementary lens for selective insertion or movement into the input beam path on an input side of the lens arrangement, the supplementary lens comprising a dispersing lens having a focal length selected for viewing the cornea, while the lens arrangement of the microscope is focused at the point of the first image.

4. The microscope according to claim 3, wherein the reversal lens system and the supplementary lens are coupled with one another at least one of mechanically, electromechanically or electronically so that the supplementary lens and the reversal lens system are only capable of alternate insertion into the beam paths and the input beam path, respectively.

5. A stereoscopic microscope comprising:

an eyepiece arrangement;

a magnification changer;

a movable reversal lens system for selective insertion or movement into two beam paths in front of or behind the magnification changer, the reversal lens system exchanging the two beam paths against one another to cause an image reversal;

a lens arrangement;

a movable supplementary lens for selective insertion or movement into an input beam path on an input side of the lens arrangement; and an insertable optic system for selective insertion or movement into the input beam path between the supplementary lens and an eye being tested for viewing of a retina.

6. The microscope according to claim 5, wherein the optic system reproduces a first image at a point for viewing with the microscope, the lens arrangement of the microscope being focused on the point of the first image.

7. The microscope according to claim 6, wherein the supplementary lens comprises a dispersing lens having a focal length selected for viewing the cornea, enabling the stereoscopic microscope to change between views of the cornea and views of the retina without focusing.

8. The microscope according to claim 6, wherein the reversal lens system and the supplementary lens are coupled with one another so that the reversal lens system and the supplementary lens are capable of simultaneous insertion into the two beam paths and the input beam path, respectively.

9. The microscope according to claim 5, wherein the supplementary lens comprises a dispersing lens having a focal length selected for viewing the cornea.

10. The microscope according to claim 5, wherein the reversal lens system and the supplementary lens are coupled with one another so that the reversal lens system and the supplementary lens are capable of simultaneous insertion into the two beam paths and the input beam path, respectively.

11. The microscope according to claim 5, wherein the lens arrangement has a focal length selected for viewing the cornea.

12. The microscope according to claim 5, wherein the optic system reproduces a first image at a point for viewing with the microscope, the supplementary lens of the microscope being focused on the point of the first image.

13. The microscope according to claim 12, wherein the supplementary lens comprises a convex lens.

14. The microscope according to claim 13, wherein the lens arrangement has a focal length selected for viewing the cornea, enabling the stereoscopic microscope to change between views of the cornea and views of the retina without additional focusing.

15. The microscope according to claim 5, wherein the reversal lens system and the supplementary lens are coupled with one another so that the supplementary lens and the reversal lens system are only capable of alternate insertion into the two beam paths and the input beam path, respectively.

* * * * *